(12) United States Patent
Russell

(10) Patent No.: US 6,528,258 B1
(45) Date of Patent: Mar. 4, 2003

(54) NUCLEIC ACID SEQUENCING USING AN OPTICALLY LABELED PORE

(75) Inventor: Terence S. Russell, Braintree, MA (US)

(73) Assignee: LifeBeam Technologies, Inc., Braintree, MA (US)

( * ) Notice: Subject to any disclaimer, the term of this patent is extended or adjusted under 35 U.S.C. 154(b) by 0 days.

(21) Appl. No.: 09/653,046

(22) Filed: Sep. 1, 2000

Related U.S. Application Data

(60) Provisional application No. 60/158,703, filed on Oct. 8, 1999, and provisional application No. 60/152,465, filed on Sep. 3, 1999.

(51) Int. Cl.$^7$ .......................... C12Q 1/68; C07H 21/02
(52) U.S. Cl. .......................... 435/6; 536/23.1; 536/24.1
(58) Field of Search ............................. 435/6; 536/24.1, 536/23.1

(56) References Cited

U.S. PATENT DOCUMENTS

| | | | |
|---|---|---|---|
| 4,962,037 A | 10/1990 | Jett et al. ........................ | 435/6 |
| 4,994,372 A | 2/1991 | Tabor et al. | |
| 5,207,880 A | 5/1993 | Middendorf et al. | |
| 5,322,796 A | 6/1994 | Ishikawa et al. | |
| 5,468,364 A | 11/1995 | Fujii et al. | |
| 5,614,503 A | 3/1997 | Chaudhary et al. | |
| 5,674,743 A | 10/1997 | Ulmer ..................... | 435/287.2 |
| 5,776,674 A | 7/1998 | Ulmer ........................... | 435/6 |
| 5,777,078 A | 7/1998 | Bayley et al. | |
| 5,795,782 A | 8/1998 | Church et al. ................ | 436/2 |
| 5,821,058 A | 10/1998 | Smith et al. | |
| 5,837,533 A | 11/1998 | Boutin et al. | |
| 5,851,765 A | 12/1998 | Koster et al. | |
| 5,872,003 A | 2/1999 | Koster et al. | |
| 5,911,952 A | 6/1999 | Tsuji et al. | |
| 5,928,869 A | 7/1999 | Nadeau et al. ................ | 435/6 |
| 5,935,791 A | 8/1999 | Nadeau et al. ................ | 435/6 |
| 6,015,714 A | 1/2000 | Baldarelli et al. ............. | 436/2 |
| 6,046,003 A | 4/2000 | Mandecki ..................... | 435/6 |
| 6,210,896 B1 | 4/2001 | Chan ............................ | 435/6 |
| 6,263,286 B1 * | 7/2001 | Gilmanshin et al. .......... | 702/19 |

FOREIGN PATENT DOCUMENTS

| | | |
|---|---|---|
| JP | 09222418 | 8/1997 |
| JP | 10019803 | 1/1998 |
| JP | WO 98/33939 | 8/1998 |
| WO | WO 98/35012 | 8/1998 |
| WO | WO 99/05167 | 2/1999 |
| WO | WO 00/09757 | 2/2000 |

OTHER PUBLICATIONS

US 5,747,249, 5/1998, Smith et al. (withdrawn)

Yin et al, "Transcription against an applied force" Science 270:1653–1656 (1995).*

Akeson, et al., "Microsecond Time–Scale Discrimination Among Polycytidylic Acid, Polyadenylic Acid, and Polyuridylic Acid as Homopolymers or as Segments Within Single RNA Molecules", *Biophysical Journal*, 77: 3227–3233, 1999.

Bruchez, et al., "Semiconductor Nanocrystals as Fluorescent Biological Labels", *Science*, 281:2013–2016.

Cescatti, et al., "Modification of Lysine Residues of *Staphylococcus aurues* α–Toxin: Effects on Its Channel–Forming Properties", *J. Membrane Biol.* 119: 53–64, 1991.

Chan, et al., "Quantum Dot Bioconjugates for Ultrasensitive Nonisotopic Detection" *Science*, 281: 2016–2018, 1998.

Chen, et al., "Permeation Through an Open Channel: Poisson–Nernst–Planck Theory of a Synthetic Ionic Channel", *Biophysical Journal*, 72: 97–116, 1997.

Dickson, et al., "Simultaneous Imaging of Individual Molecules Aligned Both Parallel and Perpendicular to the Optic Axis" *Phys. Rev. Lett.* 81: 5322, 1998.

Dörre, et al., "Techniques for Single Molecule Sequencing", *Bioimaging*, 5, 139–152, 1997.

Eggeling, et al., "Laser–Induced Fluorescence of Coumarin Derivatives in Aqueous Solution: Photochemical Aspects for Single Molecule Detection", *Bioimaging*, 5:105–115, 1997.

Eisenberg, R.S., "Computing the Field in Proteins and Channels", *J. Membrane Biol.* 150: 1–25, 1996.

Eisenberg, et al., "Diffusion as a Chemical Reaction: Stochastic Trajectories Between Fixed Concentrations", *J. Chem. Phys.* 102(4): 1767–1780.

Enderlein, et al., "The Statistics of Single Molecule Detection: An Overview" *Bioimaging*, 5: 88–98, 1997.

Enderlein, J., "Maximum–Likelihood Criterion and Single–Molecule Detection" *Applied Optics*, 34(3): 514–526, 1995.

Fields, et al., "A Novel Genetic System to Detect Protein–Protein Interactions" *Nature*, 340: 245, 1989.

Gimzewski, et al., "Nanoscale Science of Single Molecules Using Local Probes", *Science*, 283: 1683–1688, 1999.

Goodwin, et al., "Single–Molecule Detection in Liquids by Laser–Induced Fluorescence" *Acc. Chem. Res.*, 29: 607, 1996.

Gyuris, et al., "Cdi1, A Human G1 and S Phase Protein Phosphatase That Associates with Cdk2" *Cell*, 75: 791, 1993.

(List continued on next page.)

*Primary Examiner*—Jeffrey Fredman
(74) *Attorney, Agent, or Firm*—Choate, Hall & Stewart; Brenda Herschbach Jarrell; C. Hunter Baker

(57) ABSTRACT

The present invention provides a system for analyzing polymer molecules by detecting their effects on an optical agent. Certain preferred embodiments of the invention involve the analysis of polynucleotide molecules through detection of their quenching effects on a fluorescent reporter.

11 Claims, 3 Drawing Sheets

OTHER PUBLICATIONS

Ha, et al., "Probing the Interaction Between Two Single Molecules: Fluorescence Resonance Energy Transfer Between a Single Donor and a Single Acceptor" *Proc. Natl. Acad. Sci. USA*, 93: 6264–6268, 1996.

Ha, et al., "Strategy for Room Temperature Spectroscopy of Single Molecules", *Bioimaging*, 5: 99–104, 1997.

Heinemann, et al., "Open Channel Noise", VI. Analysis of Amplitude Histograms to Determine Rapid Kinetic Parameters, *Biophysical Journal*, 60: 577–587, 1991.

Jezewska, et al., "Does Single–Stranded DNA Pass Through the Inner Channel of the Protein Hexamer in the Complex with the Escherichia Cell DnaB Helicase?" *J. Biol. Chem.* 273(17): 10515–10529, 1998.

Kasianowicz, et al., "Characterization of Individual Polynucleotide Molecules Using a Membrane Channel" *Proc. Natl. Acad. Sci. USA*, 93: 13770–13773, 1996.

Kavarnos, et al., "Photosensitization by Reversible Electron Transfer: Theories, Experimental Evidence, and Examples" *Chem. Rev.* 86(2):401–450, 1986.

Köllner, et al., "How Many Photons are Necessary for Fluorescence–Lifetime Measurements?" *Chem. Phys. Lett.* 200: 199–204, 1992.

Köllner, "How to Find the Sensitivity Limit for DNA Swquencing Based Linear–Induced Fluorecence" *App. Optics*. 32(6): 806–820, 1993.

Kunkel, "Rapid and Efficient Site–Specific Mutagenesis Without Phenotypic Selection" *Proc. Natl. Acad. Sci. USA*, 82(2): 488–492, 1985.

Lin, et al., "Estimation of the Distance Change Between Cysteine–457 and the Nucleotide Binding Site When Sodium Pump Changes Conformation from $E_1$ to $E_2$ by Fluorescence Energy Transfer Measurements", *Biochemistry*, 35: 8419–8428, 8419–8428, 1996.

Mathis, et al., "Steps Towards Spatially Resolved Single Molecule Detection in Solution" *Bioimaging*, 5: 116–128, 1997.

Meller, et al., "Rapid Nanopore Discrimination Between Single Polynucleotide Molecules", *PNAS*, 97(3): 1079–1084, 2000.

Moerner, et al., "Illuminating Single Molecules in Condensed Matter", *Science*, 283: 1670–1676, 1999.

Müller et al., "Time–Resolved Indentification of Single Molecules in Solution with a Pulsed Semiconductor Diode Laser" *Chem. Phys. Lett.* 262:716–722, 1996.

Petit, et al., "Assessment of Fluorochromes for Cellular Structure and Function Studies by Flow Cytometry" *Biol. Cell*, 78:1, 1993.

Sauer, et al., "Diode Laser Based Detection of Single Molecules in Solutions" *Chem. Phys. Lett.* 254: 223–228, 1996.

Seidel, et al., "Nucleobase–Specific Quenching of Fluorescent Dyes. 1. Nucleobase One–Electron Redox Potentials and Their Correlation with Static and Dynamic Quenching Efficiencies" *J. Phys. Chem.*, 100: 5541–5553, 1996.

Sigworth, F. J. "A Test for Coupling Between Current Fluctuations and Conformational: Transitions in the Acetylcholine Receptor", *Biophysical Society*, 49: 1041–1046, 1986.

Sigworth, F.J. "Noise in Acetylcholine Receptor Currents Suggests Conformational Fluctuations", *J. Biophysical Society*, 47: 709–720.

Sung, et al., "Polymer Translocation Through a Pore in a Membrane", *Physical Review Letter*, 77(4): 783–786, 1996.

Szöll si, et al., "Application of Fluorescence Reosnance Energy Transfer in the Clinical Laboratory: Routine and Research", *Cytometry*, 34,159–179, 1998.

Trabesinger, et al., "Detection of Individual Oligonucleotide Pairing by Single–Molecule Microscropy", *Anal. Chem.* 71: 279–283, 1999.

Walker, et al., "Assembly of the Oligomeric Membrane Pore Formed by Staphylococcal α–Hemolysin Examined by Truncation Mutagenesis" *J. Biol. Chem.*, 267(30): 21782–21786, 1992.

Walker, et al., "Functional Expression of the α–Hemolysin of *Staphylococcus aureus* in Intact *Escherichia coli* and in Cell Lysates", *The Journal of Biological Chemistry*, 267(15): 10902–10909.

Walker, et al., "Key Residues for Membrane Binding, Oligomerization, and Pore Forming Activity of Staphylococcal α–Hemolysin Identified by Cysteine Scanning Mutagenesis and Targeted Chemical Modification", *The Journal of Biological Chemistry*, 270(39): 23065–23071, 1995.

Weiss, S., "Fluorescence Spectroscopy of Single Biomolecules", *Science*, 283: 1676–1683, 1999.

Youn, et al., "Fluorescence Energy Transfer Immunoassay Based on a Long–Lifetime Luminescent Metal–Ligand Complex" *Anal Biochem.*, 232: 24–30, 1995.

Common Applications For Thiol–Reactive Probes, Handbook—2.1 Introduction to Thiol Modification.

Fluorescence Resonance Energy Transfer, Handbook—Molecular Probes Literature.

Time–Correlated Photon Counting Tech Note TCSPC 1.1, The Principle of Time–Correlated Photon Counting.

Polycarbonate Screen Membranes (PCTE), Osmonics.

The Isopore Track–Etched Membrane Filter, Product Bulletin.

Seidel, et al., "Nucleobase–Specific Quenching of Fluorescent Dyes. 1. Nucleobase One–Electron Redox Potentials and Their Correlation with Static and Dynamic Quenching Efficiencies", *J. Phys. Chem.* 100: 5541–5553, 1996.

International Search Report issued for corresponding PCT application PCT/US00/24140.

* cited by examiner

NUCLEIC ACID SEQUENCING USING AN OPTICALLY LABELED PORE

PRIORITY INFORMATION

This application claims priority to U.S. provisional application U.S. Ser. No. 60/158,703, filed Oct. 8, 1999, and U.S. provisional application U.S. Ser. No. 60/152,465, filed Sep. 3, 1999. Both of these application are incorporated herein by reference.

BACKGROUND OF THE INVENTION

The present invention relates to the analysis of polymer molecules, and particularly of polynucleotides. Polynucleotides are polymeric molecules comprising repeating bases of nucleosides bound together in a linear fashion. Examples of polynucleotides are deoxyribonucleic acid (DNA) and ribonucleic acid (RNA). DNA is the genetic material of living organisms. It is the molecule that stores and transmits the code of life. Segments of DNA known as genes act as the templates for the formation of proteins, which are the molecules that comprise the structure and function of all living matter.

DNA polymers are made up of strings of four different nucleotide bases known as adenine (A), guanine (G), cytosine (C), and thymine (T). The particular order, or "sequence" of these bases in a given gene determines the structure of the protein encoded by the gene. Furthermore, the sequence of bases surrounding the gene typically contains information about how often the particular protein should be made, in which cell types, etc. Knowledge of the DNA sequence in and around a gene provides valuable information about the structure and function of the gene, the protein it encodes, and its relationship to other genes and proteins.

The complete nucleotide sequence of all DNA polymers in a particular individual is known as that individual's "genome". Whereas most bacteria have genomes on the order of a few million bases long, the human genome contains more than 3.5 billion bases. In recent years, both government and private organizations have expended enormous resources attempting to build a complete, detailed map of the human genome. In particular the Human Genome Project, a government-funded effort directed by the National Institutes of Health, has promised to deliver a complete human sequence by the year 2003 at a cost that is expected to exceed $3 billion. Private corporations have also entered into the race. For example, Celera, Inc. a Rockville, Md. company, has spent over $300 million dollars with the purpose of sequencing the genome by 2001.

There are significant reasons that so much effort and money is focused on sequencing the human genome. First, there is the obvious scientific merit associated with having a detailed map of mankind's genetic template. The information embodied by such a map will allow scientists to better understand the relationship between our genetic code and the functions of the nearly 100,000 proteins that make up our bodies. It is already known that there is a direct relationship between particular DNA sequences and certain-disease states. This fact has encouraged many pharmaceutical companies to invest heavily in the field of genomics research in the hope of discovering the underlying genetic nature of these diseases.

Another reason that sequence information is important is the expected ability to determine an individual's susceptibility to particular diseases based on his or her genetic sequence. The field of genetic diagnostics is dedicated to identifying nucleotide sequence elements whose presence in a genome correlates with development of a particular disorder or feature. The more information is available about genomic sequence elements observed in the population the more powerful this field becomes. Furthermore, the more rapidly information about the prevalence and penetrance of sequence elements in the general population, as well as the presence of particular such elements in the genomes of particular individuals being tested, the more effective the analysis becomes.

Yet another reason that sequence information is valuable is that a number of pharmaceutical companies seek to develop drugs that are custom-tailored to an individual's genetic profile. The hope is to provide targeted, potent drugs, possibly with decreased dosage levels appropriate to the genetic characteristics of the particular individual to whom the drug is being administered.

Current Sequencing Technology

Most currently available nucleotide sequencing technologies determine the nucleotide sequence of a given polynucleotide strand by generating a collection of complementary strands of different lengths, so that the collection includes molecules terminating at each base of the target sequence and ranging in size from just a few nucleotides to the full length of the target molecule. The target molecule's sequence is then determined by analyzing the truncated complementary strands and determining which terminate with each of four DNA nucleotides. A "ladder" is constructed by arranging the truncated molecules in order by length, and the terminal residue of each rung is read off to provide the complement of the target polynucleotide sequence.

The most popular DNA sequencing systems generate the collection of truncated complementary molecules by performing a template synthesis reaction in the presence of low concentrations of modified versions of each of the four natural nucleotides. These modified compounds can be added to a polynucleotide chain but cannot be extended. Furthermore, each one is labeled with a different fluorescent dye, so that chains terminated with different nucleotides can be distinguished from one another by the color of fluorescence they emit (see, for example, Smith et al., U.S. Pat. No. 5,821,058; Smith et al., U.S. Pat. No. 5,747,249; Kaiser et al., *Methods Enzymol* 218:122–153, 1992; *Automated DNA Sequencing Chemistry Guide*, PE Applied Biosystems, A division of Perkin-Elmer (1998); each of which is incorporated herein by reference). The sequence of the target molecule is then determined by reading the sequence of fluorescent colors emitted by the arranged rungs of the molecular ladder of complementary strands.

These DNA sequencing methods have been automated, and machines that perform them are available in the commercial marketplace. The most advanced of these machines are capable of carrying out the above sequencing process in parallel reactions (up to 96 at a time). Under certain conditions the output from one machine may exceed 300,000 bases per day. Using large numbers of such machines, some organizations claim sequencing rates as high as 100 million bases per day (The Economist 347(8068):87–88 May 16 1998; incorporated herein by reference).

Currently-available DNA sequencing systems are very powerful. However, they are limited by their speed, their complexity, and their cost. Because of these problems, their use is not widespread in clinical environments. For example, even the most sophisticated genetic diagnostic procedures involve the analysis of only very short regions of sequence (often not by direct sequencing but rather by indirect methods that probe the underlying sequence). Large scale sequencing of patient DNA is simply not performed in the clinic.

The speed of currently available automated sequencers is limited by the inability of the machines to analyze more than several hundred (typically around 600) nucleotides of sequence at a time. Allowing for the overlaps needed to piece together correctly strands less than 1000 bases longs, the standard sequencing process may have to be performed as many as 70 million times in order to determine the human genome sequence (Technology Review 102(2):64–68 1999 Mar/Apr; incorporated herein by reference). As has been noted, it takes many 600 s to fit into 3 billion and in practice it takes many more than that to make a full sequence because the individual fragments have to be linked together by matching up their overlaps. (*The Economist* 347(8068): 87–88 May 16 1998; incorporated herein by reference). At a theoretical rate of even 100 million bases per day it will take at least a year to sequence the human genome once. With these techniques, large-scale sequencing cannot become a clinical tool. For genetic diagnostics to become practical in a clinical setting, the sequencing rate will have to be increased by at least three to five orders of magnitude.

The complexity of current sequencing technology arises from the need to amplify and modify the genetic molecules being sequenced. This modification is carried out either chemically or enzymatically, and amplification is achieved by numerous cycles of heating and cooling. One of the more popular ways of amplifying and modifying the DNA to be sequenced is using the polymerase chain reaction (PCR). The PCR involves successive rounds of denaturing, annealing, and extension using a DNA polymerase and resulting in the exponential amplification of the original strand of DNA. The length of time associated with each part of the cycle depends on the fluid volume and the length of DNA to be amplified. Typical times are on the order of 10–30 seconds for the denaturation step, 5–30 seconds for the annealing step, and 1–4 minutes for the extension step. This cycle is usually carried out 15 to 30 times. Therefore, normal PCR times are one-to three hours depending on the length of the DNA to be amplified. The fundamental physical processes that constrain the denaturing, annealing, and labeling are the number of detectable strands needed, the time needed to carry out this process, and the processivity of the enzyme. This entire process is time consuming and requires following involved procedures. Although many of the available sequencing machines have automated much of these processes, even these machines must be operated by highly trained technicians and consume large quantities of chemicals.

In addition to the chemical complexity of traditional sequencing technology, there is also a tremendous amount of computational complexity. As mentioned above, 70 million separate and overlapping sequence fragments; each only about 600 bases long, must be pieced together to form the human genome using current sequencing technology. Numerous powerful computers, sophisticated algorithms, and highly trained computer scientists are required to carry out this task.

Finally, the cost of current sequencing systems, while not overwhelming for research needs, becomes prohibitive when considered on a scale large enough to encompass wide-spread clinical genetic diagnostics. Indeed, the current state of the art automatic sequencing system costs approximately $100,000. According to the National Human Genome Research Initiative, the current cost of producing fully confirmed sequence information is approximately $0.50 per base. To sequence an entire person would cost about 1.5 billion dollars assuming three orders of magnitude cost savings by parallelizing current technology.

Clearly, there is a need for the development of improved sequencing technologies that are faster, easier to use, and less expensive.

SUMMARY OF THE INVENTION

The present invention provides an improved system for the analysis of polymer molecules. In general, the system provides an optical agent whose detectable properties are altered by interaction or association with the polymer. In preferred embodiments, the agent's detectable properties are differentially affected by individual monomers in the polymer, so that the sequence of monomer units in a given polymer molecule may be determined by sequentially contacting the polymer's monomers with the agent, for example by passing the polymer in a linear fashion past the agent.

In preferred embodiments of the invention, the optical agent comprises a fluorescent compound whose emissions are characteristically quenched by individual monomers. In particularly preferred embodiments, a polynucleotide strand is drawn linearly past such a fluorescent agent, in sufficient proximity to allow the individual nucleotide monomers to exert their characteristic quenching effects. Analysis of fluorescent quenching over time determines the sequence of the polynucleotide molecule.

The inventive polymer analysis-techniques allow the rapid analysis of very long polymer chains at the level of a single polymer molecule. Amplification of target molecules is not required. Also, target molecules may be analyzed directly, in their native state; chemical or other modifications are not required. Certain embodiments of the invention allow the integrity of the target molecule to be preserved so that additional analyses may be performed on the same molecule whose sequence has been determined. The speed, simplicity, and effectiveness of the inventive system offer significant advantages over, currently available technologies. In certain preferred embodiments, the inventive system allows the analysis of large (greater than 1000, and preferably greater than 10,000, 20,000, 30,000, 40,000, 50,000, or 100,000 nucleotides) nucleic acid molecules at speeds of more than 1,000 bases per second and up to 100,000 bases per second.

The system can be used to analyze any type of polymer with monomer differences that can be optically detected by choosing the appropriate optical agent.

Characterization of the number of bases in a polymer (without making any distinction amongst the bases, i.e.— base counting) is also possible. In this case the optical agent need only produce a signal that indicates the presence or absence of the base. This would allow determination of the size of the polymer with single monomer accuracy.

Polarization of the light can yield information about the relative orientation of the emitting and quenching groups (Dickson et al., *Phys. Rev. Lett.* 81,: 5322, 1998; incorporated herein by reference). This method would be useful for determining the orientation of the bases as they pass by the optical agent. This method could determine whether the chemical rings are perpendicular to the backbone or how they are oriented with respect to each other.

DEFINITIONS

Figure 1:
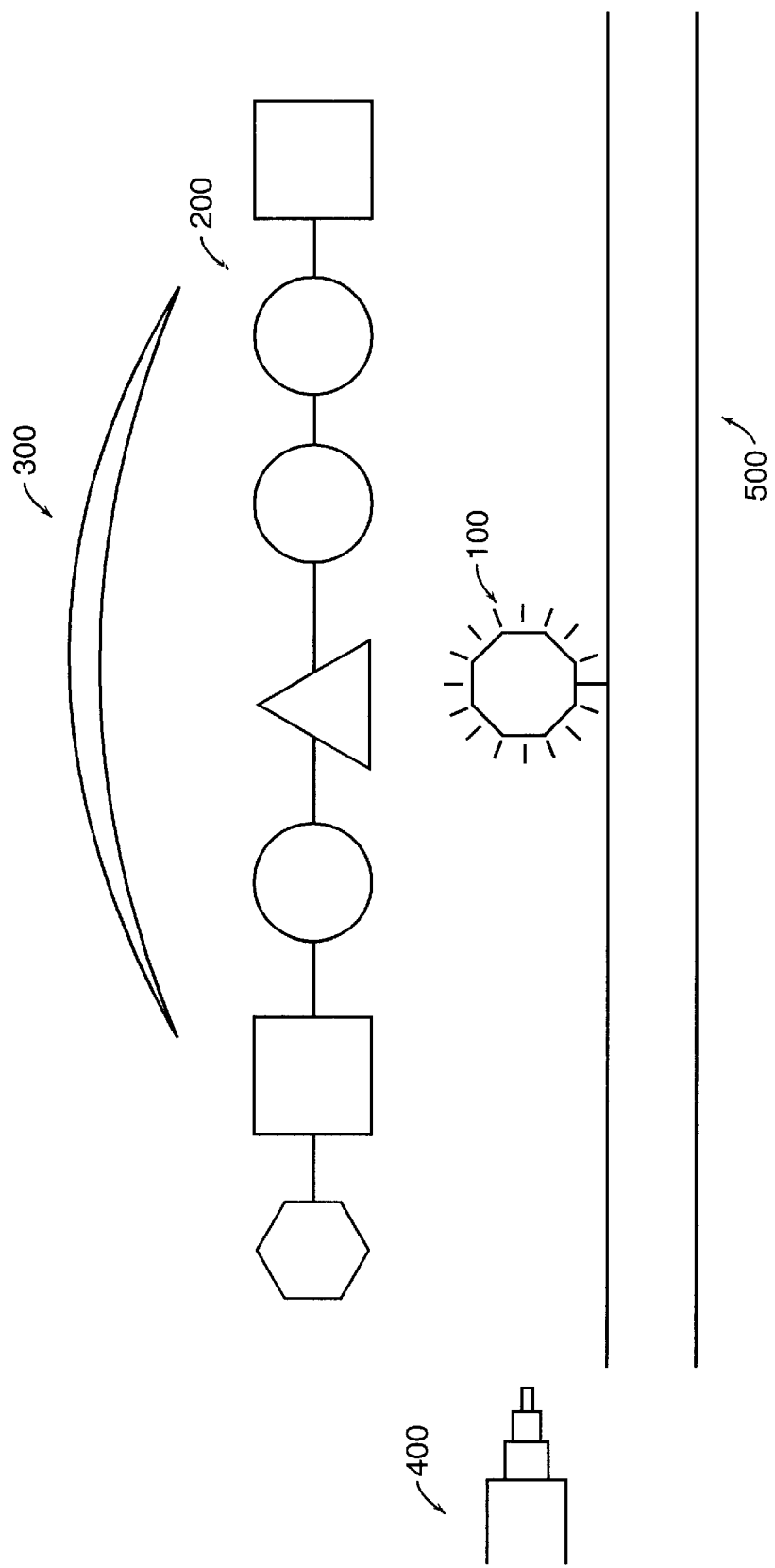
FIG. 1 is an exploded view of a polymer 200 being characterized using an optical agent 100, a device to excite the optical agent 400, a molecular scaffold to guide the monomers of the polymer 500, and a detector 300.

Association, in general, describes an arrangement in three dimensional space that allows two or more entities to interact with one another. An association may be accomplished by means of a covalent or non-covalent interaction (such as, for example, a van der Waals interaction, a hydrophobic interaction, an electromagnetic interaction, hydrogen bonding, anionic interaction, etc.). Also, an association may be direct in that two associated entities physically touch or are linked (e.g., by a covalent bond), or it may be indirect in that two associated entities are linked to one another by means of their association with other entities that touch each other.

Detection volume refers to the volume of space around an optical agent through which a monomer must pass for its interaction with the optical agent to be detected. The boundaries of the detection volume may vary with the type and mechanism of optical agent employed. For example, as discussed herein, preferred optical agents comprise fluorophores that operate either by electron transfer or by energy transfer (described in more detail below). In the case of electron transfer with its orbital overlap requirement, a sphere of interaction centered on the fluorophore is defined that has a radius of approximately 1–10 Angstroms. In the case of energy transfer, the interaction distance is approximately 10 to 100 Angstroms because the interaction is coulombic (i.e., involving an induced dipole-dipole interaction). The interaction volume is therefore constrained by the geometry of the distance between adjacent monomers (e.g., base-to-base distance of the nucleotides) and the radius of effect of the relevant process (electron or energy exchange). Ideally, the radius of the detection volume of the process should be less than the distance between adjacent monomers. For example, in double-stranded B-DNA, the base-to-base separation is only 3.4 Angstroms (Stryer, *Biochemistry 3rd Ed.*, New York: W. H. Freeman and Company, 1988). However, single-stranded DNA does not form a helix so the base-to-base distance is closer to 10 Angstroms, but this distance depends greatly on conditions such as pH, salt concentration, and temperature.

Interaction may be synonymous with association but, as will be clear from context, may refer to an association that results in a particular physical effect on one or both of the associating entities. For example, interaction of a monomer with an optical agent results in a change in one or more optical properties of the optical agent. In particular, where the optical agent comprises a fluorophore, monomer interaction with the fluorophore entails either the exchange of an electron between the fluorophore and the closest monomer or the exchange of energy via an induced. dipole-dipole interaction. In the case of energy transfer via an induced dipole-dipole interaction, the sensitivity is inversely proportional to $r^6$ so the monomer closest to the optical agent dominates the interaction between the polymer and the optical agent over the other monomers.

Nucleic acid polymer refers to a polymer of nucleotides. The polymer may consist of natural bases, chemically modified bases, biologically modified bases, intercalated bases, modified sugars, or modified phosphate groups.

Optical agent refers to a device or chemical compound. A detectable optical property of the agent changes upon interaction of a monomer of the polymer with the agent. An example of an agent would be a fluorophore whose fluorescence decay time is modified by interaction with a monomer that nearby. Preferred optical agents are differently affected by different types of monomers, so that the individual (and sequential) identities of monomers in a polymer may be assigned based on the effect exerted by the monomers on the optical agent.

Pore refers to any opening in a substrate or structure that allows the passage of a particle (or polymer) that would not otherwise be able to pass into or through such a substrate or structure. Preferred pores include, for example, those formed from assemblages of protein molecules. In particularly preferred embodiments of the invention, a natural pore is employed. Examples of natural pore-forming proteins include the voltage-dependent mitochondrial ion channel (VDAC), Gramacidin, Valinomycin, LamB (maltoporin), OmpF, OmpC, PhoE, mitochondrial porin (VDAC), and Tsx, the F-pilus. One particularly preferred embodiment, as discussed in Example 1, utilizes a pore formed from α-hemolysin proteins. Alternative preferred pores include, for example, the passages formed through materials by track-etching processes such as are described in Example 4.

BRIEF DESCRIPTION OF CERTAIN PREFERRED EMBODIMENTS OF THE INVENTION

As mentioned above, the present invention provides a system for analyzing polymers by exposing individual polymer molecules to an optical agent whose detectable properties are modified by association with the polymer. Preferably, individual monomers exert different effects on the optical agent, so that the sequence of monomers in the polymer may be detected by sequentially contacting the individual monomers with the agent and analyzing the changes in the agent's optical properties over time.

FIG. 1 presents a generalized schematic of one embodiment of the inventive system, including an optical agent 100, a polymer 200, and a detection system 300. Also depicted in FIG. 1 are an activation system 400 for stimulating the optical agent to exhibit its detectable property (e.g., fluorescence) and a mechanism 500 for controlling polymer association with the optical agent so that individual monomers are linearly presented to the agent. Each of these elements is discussed in more detail below.

Optical Agent

Any optical agent whose detectable optical property or properties is/are modified by association with a polymer molecule may be employed in the practice of the present invention. Preferably, the agent is differentially affected by individual monomers of the polymer so that the monomer sequence may be determined by presenting the polymer's monomers to the agent in linear order and analyzing the changing effects on the agent over time.

Preferred optical agents for use in accordance with the present invention comprise fluorescent elements that are quenched by exposure to a polymer. An extensive literature is available describing fluorescence and the types of compounds that exhibit this behavior, as well as the particular properties (e.g., fluorescence decay time, absorbance spectra, emission spectra, photostability, and quantum efficiency) of these compounds (see, for example, Gilbert et al., *Essentials of Molecular Photochemistry*, CRC Press, 1991, incorporated herein by reference; see also Appendix A). Detailed descriptions of fluorescence quenching are also available (see, for example, Gilbert et al., *Essentials of Molecular Photochemistry*, CRC Press, 1991; Kavarnos et al., *Chem. Rev.* 86:401, 1986; Wagoner, *Methods Enzymol.* 246:362, 1995; Millar, *Curr. Opin. Struct. Biol.* 6:637, 1996; Petit et al., *Biol. Cell* 78:1, 1993; each of which is incorporated herein by reference).

An excited state molecule (known as the sensitizer) by itself may simply emit fluorescent radiation with a characteristic intensity and time dependence and return to its ground state. However, when a reactive molecule (known as a quencher) is present, alternative reaction pathways are possible. The quencher may absorb some of the energy from the sensitizer, thereby reducing the sensitizer's emission intensity and increasing the sensitizer's fluorescence decay rate. Therefore, the quenching of a fluorescent emission involves a modification in the decay time of the emitting group. Measuring the fluorescence intensity and time decay directly correlates with the reaction rate of the sensitizer and its quencher. Such information provides detailed information about both molecules (Gilbert et al., *Essentials of Molecular Photochemistry*, CRC Press, 1991; incorporated herein by reference).

Two general mechanisms exist for fluorescence quenching: electron transfer and energy transfer. Quenching by electron transfer occurs when one electron jumps from an occupied orbital of one reactant to an unoccupied orbital of the other. The sensitizer's excited state can be an electron donor or acceptor.

Quenching by energy transfer is further described by two different pathways: electron exchange and dipole-dipole interaction. In the electron exchange interaction, two single electron transfers occur—one in each direction—and result in the formation of the sensitizer's ground state and quencher's excited state. Energy transfer by the dipole-dipole interaction operates by Coulombic resonance, where oscillating electrons of an excited state sensitizer are coupled with those of the quencher by an induced dipole interaction.

Since electron transfer and energy transfer by electron exchange only occur with sufficient orbital overlap, the interaction distance is less than 10 Angstroms. However, Coulombic energy transfer is effective from less than 10 to 100 Angstroms (Kavarnos et al. 1986).

In recent years, there has been much progress made in the detection of single fluorescent molecules (see, for example, Mathis et al., *Bioimaging* 5:116–128, 1997; Ha et al., *Proc. Natl. Acad. Sci. USA* 93:6264–6268, June 1996; Goodwin et al., *Acc. Chem. Res.* 29:607, 1996; Müller et al., *Chem. Phys. Lett.* 262:716, 1996; Sauer et al., *Chem. Phys. Lett.* 254:223, 1996; each of which is incorporated herein by reference). Such molecules possess characteristic fluorescence decay times that are sensitive to the molecule's electronic environment and therefore can be quenched by association with polymers that alter the environment.

Desirable fluorophores for use in accordance with the present invention are photostable under the conditions of the inventive assay, change in a unique manner upon interacting with each type of polynucleotide base, have a sufficient overall lifetime to survive the detection assay, and are excited by electromagnetic wavelengths that do not damage or destroy the components of the inventive system. Particularly preferred fluorophores would be excited by photons having a wavelength of approximately 650 nm, since inexpensive lasers are available at that wavelength.

The minimum necessary photostability is parameterized by the smallest number of photons necessary to build up a detectably different fluorescent lifetime for each polymer base. Photostability lifetime is the inverse of the average number of photons that a particular fluorescent species may emit in a given environment. For example, quantum dots, under equal conditions as the organic fluorophore Rhodamine 6G (R6G), have a photostability half life of 960 seconds compared to 10 seconds for R6G (Chan et al., *Science* 281:2016–2018, 1998; incorporated herein by reference).

The limits on the spectra will be governed by the excitation source, the absorbance properties of the optical agent, the fluorescence emission spectrum of the optical agent, and the spectral sensitivity of the detecting element. Again, in the case of quantum dots the spectral absorbance can be adjusted from 400 nm to 2 microns with sharper emission widths (full width half max (FWHM)) than organic fluorophores. (e.g., in same case as above, quantum dot vs. R6G, the FWHM peaks were 12 nm and 35 nm, respectively).

Also, it is generally preferred that the fluorophore be quenched through an electron transfer mechanism rather than an energy transfer mechanism, since electron transfer does not require the absorbance spectrum of the quencher to overlap with the emission spectrum of the fluorophore.

Clearly, the selection of fluorophore for any particular application of the present invention will be influenced by the particular type of polymer being analyzed. For any given polymer, those of ordinary skill in the art will readily be able to screen existing fluorophores to identify those that are appropriately quenched by association with the given polymer. In general, preferred fluorescent compounds include, for example, quantum dots (Chan et al., *Science* 281:2016–2018, 1998; Bruchez et al., *Science* 281:2013–2016, 1998; each of which is incorporated herein by reference).

The selection of fluorophore may also be influenced by the other components of the assay system of the present invention. For example, if the assay includes biological compounds such as proteins, it will generally be desirable to employ fluorophores with long-wavelength absorption and emission in order to avoid problems associated with autofluorescence of biological samples. [Ru(bpy)$_2$(phen-ITC)]$^{2+}$ (Young et al., *Anal Biochem* 232:24–30, 1995; incorporated herein by reference) is but one example of a preferred, long wavelength fluorophore that could be used in accordance with the present invention.

As mentioned above, preferred fluorophores are differentially affected by individual monomers of the given polymer molecule being analyzed. Such discriminating fluorophores are preferably characterized by lifetimes long enough to allow the collection of a sufficient number of photons to allow accurate assignment of the fluorophore-monomer interaction. At least one fluorophore that is differentially quenched by individual nucleosides has been reported in the art (Seidel et al., *J. Phys. Chem.* 100:5541–5553, 1996, incorporated herein by reference). In particular, these authors report that Coumarin-120 shows different fluorescent decay times (G: 1.9 ns, A: 5.3 ns, C: 4.4 ns, T: 2.3 ns) in the presence of different nucleosides, and in the absence of nucleosides (4.9 ns). The observed effects are explained by noting that, depending on the redox properties of the fluorophore in question, the quenching efficiencies of the nucleosides depends on their electrochemical oxidation potential. In light of this information, those of ordinary skill in the art could readily identify other fluorophores (e.g., by testing those in Appendix A) with the ability to discriminate among nucleoside bases on the basis of their quenching effects.

Other types of fluorescent molecules that may be used are CPM, the Alexa series of fluorescence markers from Molecular Probes, Inc., the Rhodamine family, Texas Red, and any other dyes that meet the requirements described above.

The inventive optical agent may include one or more than one particular compound whose optical propert(ies) is/are detected. Also, more than one different optical property may be analyzed. Where the optical agent includes one or more fluorophores, it preferably includes between about 1 and 10 individual fluorophores.

Additional fluorophores may either be the same or different than the original fluorophore. If the same fluorophore, then the advantage may be increased signal. Photodestruction is decreased because only one fluorophore can absorb a particular photon. So for the same number of photons as in the single fluorophore case per unit time it will take longer to destroy a particular fluorophore in the multi-optical agent case. This implies that it may be possible to increase the overall data collection time with multiple fluorophores. Again this is only if all of the added fluorophores are probing the same monomer during the same measurement interval. Otherwise there will be an overlap in the signal from identical fluorophores probing different monomers which would be difficult to resolve. However, if the additional fluorophores that are added interact in a different way with the monomers (i.e., are excited by different wavelengths or are quenched in different ways by different monomers) then by either using different excitation sources or by measuring the emitted light through different sets of filters it may be possible to simultaneously collect data on multiple optical agent-monomer interactions. In this case the additional optical agents may be added such that they probe the same monomer at the same time or such that they probe different bases at the same time. Care should be taken to distinguish signals from each type of fluorophore.

It is also possible to combine both of the above scenarios by adding multiple copies of different types of fluorophores. In this case, each member of a certain type of fluorophore must probe the same base at the same time. However different groups (composed of identical copies) of fluorophores may probe different bases at the same time.

Polymer

The present invention may be used to analyze any polymeric molecule or collection of polymeric molecules. The invention is particularly useful for the analysis of polymers made up of different, distinguishable, monomer units, and is especially well suited for the analysis of nucleic acids. One of the particular advantages of the present invention is its ability to determine long (greater than 1000, and preferably greater than 10,000, 20,000, 30,000, 40,000, 50,000, or 100,000 or more nucleotides) sequences for a nucleic acid polymer.

Association of Polymer and Optical Agent

The inventive system operates when the polymer to be analyzed is brought into sufficient proximity with the optical agent that one or more optical properties of the agent is detectably altered. For example, where the optical agent comprises a fluorophore whose fluorescence is quenched upon exposure to the polymer, the interaction volume should be that volume inside a sphere of radius r centered on the optical agent, where r is less than the base to base separation in the polymer. This guarantees that during a particular measurement interval only one base will have a dominant effect on the optical agent.

If the quenching occurs by electron transfer, the polymer should be sufficiently close to the fluorophore to allow the necessary orbital overlap (i.e., less than 10 Angstroms). For example, if one uses a coumarin, where the size is about 5–10 Angstroms, to probe a monomer (e.g., a nucleotide residue) that is about the same size and is separated by about the same distance from its neighbor in the polymer, a unique interaction should be guaranteed. Polymers (e.g., proteins), in which the monomer-to-monomer separation distance is larger, should be relatively easy to probe with small fluorescent molecules. Any structure sufficient to achieve the necessary association of polymer and optical agent may be employed in the practice of the present invention.

In general, the present invention may employ a molecular scaffold that guides or otherwise participates in association of the monomers with the optical agent. For example, the molecular scaffold may comprise a membrane, a nanostructure, or a pore. Alternatively or additionally, the invention may employ a physical or natural force (e.g., an electric attraction, a magnetic attraction or a mechanical force) to facilitate or achieve association of monomers with the optical agent. The molecular scaffold may be comprised of any available material. In certain preferred embodiments, the molecular scaffold may comprise one or more proteins, polypeptides, or other preferred biological molecules including, for example, molecular motors comprising actin, myosin, dynein, tubulin, microtubules, or kinesin. Where the molecular scaffold comprises one or more proteins, they may have structures as found in nature or have one or more modifications (changes in amino acid sequence, glycosylation, phosphorylation, chemical modifications, etc.). Methods of introducing such modifications to a protein are well known in the art.

As already discussed, certain preferred embodiments of the invention involve the serial presentation of the polymer's building blocks to the optical agent. Any structure or set of conditions that accomplishes such serial presentation may be utilized. It will be appreciated that the monomers need not be in polymerized form when they are presented to the optical agent. Of course, where the desire is to determine the sequence of monomers making up the polymer, the monomers, whether or not they are in polymerized form, must be presented in the order in which they occur in the polymer.

Many preferred embodiments of the invention involve the analysis of polymers comprising nucleic acids. As discussed in more detail in the Examples, any of a variety of mechanisms may be employed to accomplish association of a nucleic acid molecule with an optical agent, and in particular to accomplish serial presentation of monomer components. For example, it will often be desirable to utilize an electric current to move a nucleic acid molecule in space. Because nucleic acids are negatively charged, they are attracted to positive poles and can be moved (e.g., past an optical agent) on the basis of that attraction.

In one preferred embodiment of the invention, a nucleic acid molecule is moved past an optical agent, within the detection volume of the optical agent, through the combined action of an electrical pull and guidance of a pore structure to which the optical agent is linked so that passage of the nucleic acid along or through the pore brings the nucleic acid into the detection volume of the optical agent. Preferred pores include those formed from assemblages of protein molecules. In particularly preferred embodiments of the invention, a natural pore is employed. Examples of natural pore-forming proteins include Gramacidin, Valinomycin, LamB (maltoporin), OmpF, OmpC, PhoE, mitochondrial porin (VDAC), and Tsx, the F-pilus. One particularly preferred embodiment, as discussed in Example 1, utilizes a pore formed from α-hemolysin proteins. These proteins may contain one or more structural modifications as compared with the form of the protein that is found in nature. Alternative preferred pores include those formed by track-etching, as described, for example, in Example 4.

Alternative preferred embodiments of the invention utilize biological machines that are specifically adapted to bind to and/or move nucleic acids past the optical agent within the detection volume of the agent. For example, a variety of processive enzymes, including polymerases, ribosomes, exonucleases, etc., that are capable of translocating nucleic acid molecules exist.

Those of ordinary skill in the art will readily appreciate that it will often be desirable to physically associate the optical agent with the structure that controls or modifies polymer movement. Any form of physical linkage, whether direct or indirect, may be employed in the practice of the present invention so long as it is sufficient to associate the optical agent with the polymer as described herein. For example, the optical agent may be linked by a covalent or non-covalent (e.g., based on hydrogen bonds, ionic interactions, van der Waals forces, magnetic interactions, hydrophobic interactions, etc., including combinations of these) interactions. Covalent interactions are generally preferred. Any linkage known in the art may be utilized. Example 1 presents just one preferred embodiment that is particularly useful for linking fluorescent compounds or other optical agents to structures including proteins.

Additionally or alternatively, the invention may employ a ligand/receptor type interaction to indirectly link the optical agent to the molecular scaffold. Any ligand/receptor pair with a sufficient stability and specificity to operate in the context of the inventive system may be employed. To give but one example, the optical agent may be linked or associated with biotin, and the scaffold be associated with avidin. The strong binding of biotin to avidin would then allow for association of the optical agent with the molecular scaffold. One skilled in the art would realize that, of course, the biotin could be associated with the scaffold, and the avidin associated with the optical agent, and thereby, the same result would be achieved. Other possible ligand/receptor pairs include nickel ion/poly-histidine, antibody/antigen, monoclonal antibody/antigen, nucleic acid/nucleic acid binding protein (Fields et al., *Nature* 340:245, 1989; Gyuris et al., *Cell* 75:791, 1993; each of which is incorporated herein by reference), complementary strands of nucleic acids, FK506/FK506-binding protein (FKBP), rapamycin/FKBP, cyclophilin/cyclosporin, and glutathione/glutathione transferase. Those skilled in the art would also appreciate many other embodiments of this idea. Such indirect linkages are reversible. One advantage of reversible linkages is that the fluorophore can be readily replaced after its lifetime has expired:

Detection System

Clearly, the detection system utilized in the practice of the present invention will depend on the particular optical property being assayed. Any detection system capable of detecting a change in optical property of the optical agent on the time scale of the monomer-optical agent interaction may be employed. Preferably, the detection system is employed with an optical agent that discriminates among different monomers and is sufficiently sensitive to detect the differences in monomer-optical agent interactions. As discussed herein, preferred embodiments of the invention utilize fluorescence. A variety of systems for-exciting and detecting fluorescent signals are well known in the art and can readily be applied by those of ordinary skill to the practice of the present invention. Furthermore, those of ordinary skill will readily appreciate various desirable parameters or modifications of these systems. For example, in order to reduce photobleaching of the fluorophore, one may enhance the detection sensitivity of the emitted fluorescent light by: low light collection, high numerical aperture (N.A.) objectives, and the widest emissions bandpass filters that are compatible with satisfactory signal isolation.

Recent work has generated advances in the production of low-cost pulsed diode lasers that cover a wider range of wavelengths and would be particularly useful as a fluorescence activation source according to the present invention. These lasers may be used, for example, in combination with fast, sensitive photon detectors and timing electronics to detect the fluorescence lifetime of a single fluorophore (see, for example, Muller et al., *Chem. Phys. Lett.* 262:716, 1996; Sauer et al., *Chem. Phys. Lett.* 254:223, 1996; each of which is incorporated herein by reference).

Detecting elements include photomultiplier tubes (PMT), microchannel plates (MCP), and avalanche photodiodes.

Photomultiplier tubes usually operate between blue and red regions of visible spectrum with greater quantum efficiency in blue-green regions and maximum quantum efficiencies are about 25%. PMTs are well suited for work in the ultraviolet, visible, and near infrared and can handle count rates up to 1–10 Mcps.

Microchannel plates sometimes perform better than a PMT. MCPs are an array of glass capillaries coated with electron-emissive material at high voltage.

Avalanche photodiodes are solid state versions of PMTs. They usually work in red to infrared parts of spectrum and are usually used for low light detection (<1 pW) They can be used to detect single photons (in so-called Geiger-mode) and are called SPAD (single photon avalanche photo diodes). They have timing accuracy <200 ps with detection probabilities up to 50% noisier than PMTs but with greater quantum efficiency up to about 80%.

As discussed herein, particularly preferred embodiments of the present invention involve sequencing polymer molecules by detecting monomer-specific optical changes. Such embodiments preferably utilize a detection system that is capable of recording time-dependent changes in one or more detectable properties of the optical agent. For example, where the optical agent comprises a fluorophore and its measurement involves detection of fluorescence quenching, time-dependent intensity profiles are preferably detected. A variety of techniques for such detection are known in the art. For example, Time-Correlated Single Photon Counting (TCSPC) is based on the repetitive and precisely timed detection of single photons from the fluorescence signal. The reference for the timing is the corresponding fluorescence excitation pulse. A Single Photon Avalanche Photodiode (SPAD) or Photomultiplier Tube (PMT) is used to detect the emitted photons. By insuring that the probability of registering more than one photon per excitation cycle is low, the histogram of photon arrivals per time bin represents the time decay one would have obtained from a single shot time-resolved analog recording.

For effective use of TCSPC, the pulse rate must be such that 1 to 5% of the rate generates at maximum 2 to 8 Millions counts per second (Mcps), as this is the current maximum number of cps that can be handled by modern integrated single-board TCSPC solutions. Also currently available PMTs can handle up to 1 to 10 Mcps. Dead time (time that the system cannot register new photon arrivals) is preferably minimized. PMTs and SPADs may have time uncertainties of 200 to 400 ps (FWHM).

Arrays

The inventive polymer analysis system is well suited to high-throughput presentations such as arrays of assay chambers. For example, inventive assay/detection systems may be arranged in wells in a multi-well array analogous to standard arrays such as 96 well plates. The detection apparatus may then be designed and arranged to simultaneously record information from all wells, or to scan along individual wells that are read separately.

For example, where the optical agent comprises a fluorophore, both an excitation source and a detection system are required. In some embodiments of the invention, the excitation source comprises a single source (e.g., a laser) whose focus point is adjusted through the use of one or more mirrors so that the entire array may be individually scanned. In alternative embodiments, the excitation source comprises multiple lasers focused on individual wells. It is not necessary to have one laser per well; fewer lasers may be employed and then scanned along subsets of wells.

In preferred arrayed embodiments of the invention that utilize a fluorescent optical agent, individual detectors are provided for each well in the array. For example, a fiber optic system may be employed that provides individual fibers to each well. Alternatively or additionally, a . single detection system may be utilized that scans the array, for example monitoring individual wells separately. As yet another alternative, a single detector can be employed for the entire array if it has sufficient sensitivity to detect and distinguish the fluorescence in individual wells.

These and other aspects of the present invention will be further appreciated upon consideration of the following Examples, which are intended to illustrate certain particular embodiments of the invention but are not intended to limit its scope, as defined by the claims.

EXAMPLES

Example 1—Sequencing a Nucleic Acid by Passage Through an α-Hemolysin Pore with Associated Fluorescent Reporter Group This Example describes one preferred embodiment of the invention, in which the nucleotide sequence of a single stranded DNA molecule is determined by passing the DNA molecule through a biological pore formed by the α-hemolysin protein obtained from the bacterial species *Staphylococcus aureus*. Others have attempted to sequence DNA by measuring conductance changes associated with passage of the DNA polymer through a similar pore (see, for example, Church et al., U.S. Pat. No. 5,795,782, incorporated herein by reference), but the success of this approach has not yet been demonstrated. Furthermore, the physical constraints and requirements of that system (e.g., requirement of two separate fluid reservoirs) that are specific to conductance measurement are not applicable to the present invention.

In brief, this embodiment of the present invention involves the production of a modified α-hemolysin protein into which a particular cysteine residue has been engineered. This modification allows the protein monomer to be labeled with one or a number of fluorescent reporter groups (FRGs). Once bound to the pore, the FRG possesses a particular fluorescence decay time. After modification, the protein monomer is combined with non-modified, WT alpha-hemolysin monomer. The combination of recombinant and wild type monomers then assembles to form a pore embedded in a lipid bilayer. The lipid bilayer separates two fluid-filled volumes. The assembled pore allows fluid and particles smaller than the inner pore diameter to pass from one volume to the other. The fluid-filled volumes contain a buffer with salt ions. When a transmembrane voltage is applied to the system, the salt ions flow from one volume, through the pore channel, into the other volume, thereby forming a measurable current. The number of pores present contribute equally to the current. Therefore, the presence of a single pore may be confirmed by measuring the current. When single stranded polynucleotides (e.g., DNA or RNA) are added to one side of the system and a voltage is applied, the polynucleotides (which have a diameter less than the inner diameter of the pore) pass from one volume through the pore into the other volume. At the same time, a pulsed laser is focused onto the volume containing the FRG. The laser pulse excites the fluorescence reporter group (located in or near the inner pore channel), and the fluorescence decay time is recorded. By measuring the unique change in decay time of the FRG, as it interacts with different types of bases, an accurate sequence of the polynucleotide can be determined.

Particular methods associated with this embodiment of the invention are presented in more detail below.

Recombinant α-Hemolysin Production

Wild type (WT) alpha-hemolysin contains no native cysteine amino acid residues. However, alpha-hemolysin can be modified using oligonucleotide directed mutagenesis such that any residue or number of residues can be replaced with a cysteine residue(s). Replacement of a single residue with a cysteine group will provide a unique binding site for probes that are specially designed to react with thiols. Although it has been shown that certain single-cysteine mutations can diminish or disable pore formation in alpha-hemolysin (Walker et al., *J. Bio. Chem.* 270:23065, 1995; incorporated herein by reference), the same work indicates that pore formation proceeds normally for the majority of mutations. For example, a mutation at either aspartic acid 128 or at glycine 130 preserves pore formation as well as the transmission of a transmembrane current.

Mutants of alpha-hemolysin may be produced in the same manner as described in the above reference (Walker, 1995, supra). These mutations are made from the plasmid pT7-NPH8S, which encodes the wild-type sequence of alpha-hemolysin as secreted by *Staphylococcus aureus*. pT7-NPH8S is made from pT7-NPH8 (Walker et al., *J. Biol Chem.* 268:21782–21786, 1992; incorporated herein by reference) by using oligonucleotide-directed mutagenesis to correct the mutation Ser-217-Asn, that occurred during an earlier PCR. These procedures are themselves modifications of previous work (Kunkel, *Proc. Natl. Acad. Sci. USA* 82(2):488–492, 1985; incorporated herein by reference). Two examples of recombinant α-hemolysin produced by this technique are D128C and G130C. Cysteine mutations may also be produced at any other site, preferably in those sites that are exposed to the inside of the pore channel once the pore has fully assembled. However, such mutations must allow for proper pore formation and insertion into the lipid bilayer. Large-scale production of the recombinant monomers may be carried out by expression in bacteria, yeast, or other eukaryotic cells, using methods known to those skilled in the art.

FRG Selection and Attachment to D128C or G130C

There are a number of organic and organometallic molecules that may be used as fluorescence reporter groups (FRGs) in the invention. However, for this example, either 7-diethylamino-3-(4'-maleimidylphenyl)-4-methylcoumarin (CPM) or Alexa 594 C5 Maleimide is chosen (product numbers D-346 and A-10256. respectively, available from Molecular Probes, Inc.), although each fluorophore requires a different excitation source (see Excitation and Detection of Fluorescence section below). Either of these molecules may be bound to the thiol group present in the cysteine residue in D128C or GI30C via a maleimide chemical reaction (see Molecular Probes, 1999). Another possible choice of an FRG is Coumarin-120. However, additional chemical steps must be performed to insure that it binds exclusively to the chosen cysteine site.

Sample Chamber Design

A layer of insulating material with very high capacitance (e.g., material such as PFTE) separates two volumes, volume A and volume B. A hole, 1–50 microns in diameter, is then formed in the material. The hole may be formed by laser ablation or by electrical breakdown of the separating material or by some other method. The hole should be smooth enough to reduce the local surface tension around the edges of the hole, thereby allowing lipids (applied in a later step) to form a bilayer. The thickness of the material should be less then the diameter of the hole to minimize the access resistance (measured in a later step). Large access resistances will prevent the polynucleotides from entering the detection volume.

The above sample chamber design insures that the pore-FRG complex lies within a 1 micron diameter radius (the diameter of the lipid bilayer). Allowing for the fact that bilayer lipid membranes may fluctuate in height by a certain small amount (a fraction of the diameter), it is possible to design an optical detection system that focuses on the above delineated 1 femtoliter volume.

Addition of Buffer and Bilayer Formation

To each volume is then added a buffering fluid. The fluid in-each volume may be identical or different but the preferred embodiment allows for identical solutions of potassium chloride buffer to be added to both sides (1.0 M KCl, 10 mM HEPES, and pH 7.5). The hole separating the two fluid-filled volumes is then covered with lipids such that a membrane bilayer is formed. One possible method is to add 1 microliter of diphytanoyl-PC lipids (Avanti Polar Lipids) at a concentration of 25 mg/ml in anhydrous hexadecane (Aldrich Chemical Co.). The resulting bilayer prevents the movement of fluid or particles from volume A to volume B. A method for confirming that a bilayer is present is a capacitance measurement. This may be accomplished using techniques and an apparatus familiar to those skilled in the art of electrophysiology. An example of such an apparatus is the Axopatch 200B patch-clamp amplifier from Axon Instruments, Inc. A typical values for this example is 0.7 microfarads per square cm of the lipid bilayer.

Addition of Protein and Pore Formation

Once a stable bilayer is confirmed to exist one microliter of a diluted (0.04 mg/ml) toxin solution of monomers of the recombinant and WT ($\alpha$-hemolysin are added to the buffer in volume A. The toxin solution should have a 6:1 ratio (by number) of WT monomers to recombinant monomers. This ratio is chosen to increase the probability that a pore forms which contains only one FRG. These monomers will combine to form a pore, 1–2 nm in diameter, that inserts into the lipid membrane. It is now possible for fluid, certain ions, and small particles (having an effective diameter less than the inner diameter of the pore) to flow from volume A to volume B. Since the buffer added to each volume in this embodiment is composed of an ionic solution, it is possible to measure a current of ions flowing from volume A to volume B in the presence of an applied transmembrane electric potential. This measurement may be made by placing a positive electrode in volume B and a negative electrode in volume A. When a voltage of 120 mV is applied across the electrodes, a transmembrane electric field is created. The resulting ion current that flows may be measured by the same apparatus used above to confirm the presence of a bilayer. The resulting current should be approximately 120 pA. When there is no pore in the membrane, no current flows because the lipid bilayer acts as a barrier. However, when the pore forms and inserts into the lipid membrane, the current (in the form of ions) flows from one volume to the other.(depending on the orientation of the electric field and the type of ions used). Under a steady state electric field this current is approximately quantized. That is, each pore that inserts contributes an almost identical amount of current to the total measured current. By adding a sufficiently dilute amount of recombinant and WT alpha-hemolysin monomers to volume A, it is possible to reduce the rate of pore insertion to less than 1 every 30 minutes. Monitoring the current is a technique for confirming that only one pore is present. Once one pore inserts, the fluid in volume A may be replaced by perfusing with the buffer solution using standard equipment and techniques. This removes any unformed pores and reduces the chance of additional pore. Current measurements and the above perfusion insure that there is only pore channel through which fluid and particles may move from one side of the device to the other. The system is now ready for the addition of polynucleotide.

Addition of Polynucleotides

Polynucleotides may now be added to volume A of the system. Single polynucleotides travel along the electric field lines generated by the applied transmembrane voltage and enter the pore. Since the inner diameter of the pore is only slightly larger than the diameter of a single stranded polynucleotide, this process insures that the polynucleotides pass in a linear fashion through the pore. The pore's size and the size of a typical nucleotide base also assure that each base on each strand of polynucleotide that passes through the pore must pass less than 1.0 nm from any amino acid residue lining the pore channel. In addition this geometry localizes the polynucleotide in time since the polynucleotide proceeds in a stepwise fashion through the pore. This rate may be varied by adjusting parameters such as, but not limited to, the applied voltage, sample chamber geometry, and properties of the buffer (e.g., type of ions present, pH, viscosity, etc.). With the buffer, applied voltage, and sample chamber design described in (Kasianowicz et al., *Proc. Natl. Acad. Sci UREA* 93:13770–13773, 1996; incorporated herein by. reference), polynucleotide base transit times (i.e., the average time it takes for a base to pass a particular point along the channel) are on the order of a few microseconds per base. However, by modifying the buffer (e.g., by adjusting its viscosity) it is possible to slow the transit time to greater than 100 microseconds per base. Slowing the base transit time may be useful in allowing a detection system to gather more photons per base transit time and assure correct base discrimination.

When a strand of single stranded polynucleotide enters the pore, the measured current drops by over 90% (Kasianowicz et al., *Proc. Natl. Acad Sci USA* 93:13770–13773, 1996; incorporated herein by reference) and stays low until the polynucleotide has exited the pore into volume B. The drop in current may be used to trigger the excitation and detection system and its accompanying electronics. Similarly, the rise in current that follows may be used to stop the excitation/detection cycle.

Excitation and Detection of Fluorescence

Once it is confirmed that only one pore is present and that it is successfully passing polynucleotides, the system is ready for the fluorescence excitation/detection process. Determining the number of fluorescent markers present in the system and their decay times may be performed using techniques familiar to those in the field of single molecule detection.

Figure 2:
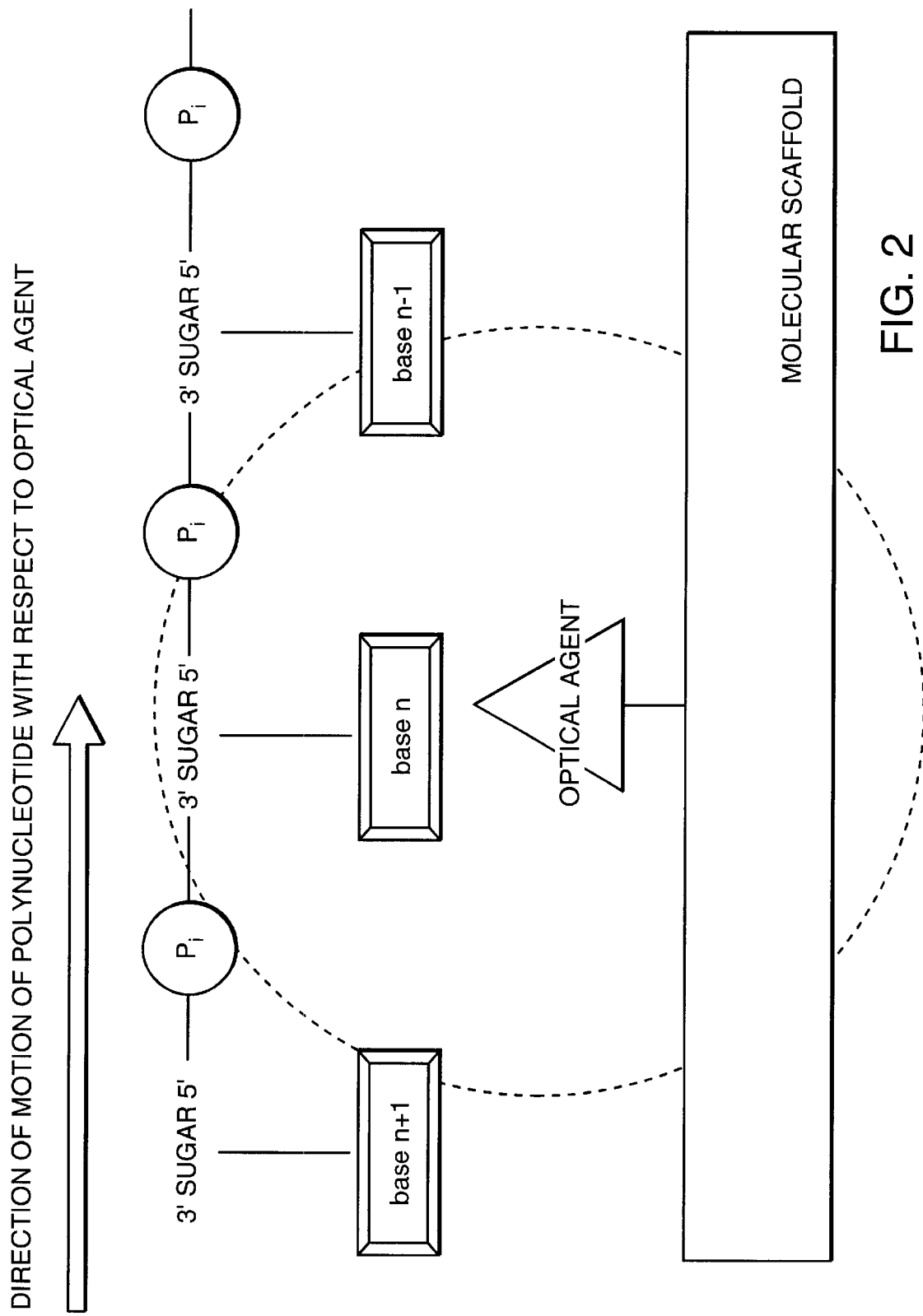
FIG. 2 is an exploded view of DNA bases passing within the detection volume of the optical agent attached to a molecular scaffold.

For the FRG and molecular scaffold described above, the following excitation/detection and TCSPC system is used to initiate and detect the fluorescence decay time (see FIG. 2). This system consists of a pulsed diode laser system with an emission wavelength that is compatible with the fluorescence absorbance properties of the FRG. In the case of Coumarin-120 or CPM, which have fluorescence absorbance maxima near 394 nm, the excitation source is a blue picosecond diode laser (LDH400 PicoQuant, Gmbh, Berlin, FRG) with an emission wavelength of 390 nm. This laser head may be driven by a PDL 800 Diode laser driver (PicoQuant) and may be pulsed up to 40 MHz. The laser driver also provides the electric sync signal needed for the photon arrival time measurement. This signal passes directly to the TCSPC electronics via a 50 Ohm cable. The excitation laser light is attenuated by a neutral density filter to prevent detector saturation and insure that the number of registered photons per cycle is low. It is then focused onto the 1 femtoliter sample volume using appropriate optics. As mentioned above, the single labeled pore is constrained to be within this detection volume. After absorbance the FRG emits a wavelength of light that is longer than the excitation light. To exclude polarization effects, the fluorescence of the probe should be observed in a conventional 90 degree setup with a polarizer set to the magic angle of 54.7 degrees. A cutoff filter eliminates scattered light. The filtered light is then collected with a 1.4 numerical aperture objective lens and focused onto a PMT or SPAD. The electrical signal from the detector is fed into the TCSPC electronics (SPC-530 from PicoQuant, GmBh), located on a single board that is inside of a Pentium PC. This device can collect a new histogram up to every 100 microseconds. Fluorescence decay curves should be fit using a least-squares fit in terms of a sum of exponentials (e.g., Marquat's algorithm). The quality of the fit may be judged by weighted residuals, an autocorrelation function, and the reduced chi-squared.

Reporter Group Excitation and Base-Specific Interaction

The time scales in the fluorescence decay of organic fluorophores range from hundreds of picoseconds to a few nanoseconds. In particular, the coumarin FRGs mentioned above (CPM and Coumarin-120) have fluorescence decay times on the order of a few nanoseconds in an aqueous environment. In order to form an accurate decay time histogram, an interval equal to 10 times the fluorescence decay time must be monitored. This corresponds to approximately 50 ns for coumarin-120. Therefore at a polynucleotide base transit rate of 10 microseconds per base it should be possible to gather 2000 fluorescence decay histograms per base. Based on calculations made by others, this is more than enough data to uniquely identify the transiting base (Koblner et al., *Chem. Phys. Lett.* 200:199–204, 1992; Köllner *App. Optics* 32(6):806–820, 1993; Enderlein et al., *Bioimaging* 5:88–98, 1997; each of which is incorporated herein by reference).

Example 2—Sequencing a Nucleic Acid in a Single-Chamber System

Figure 3:
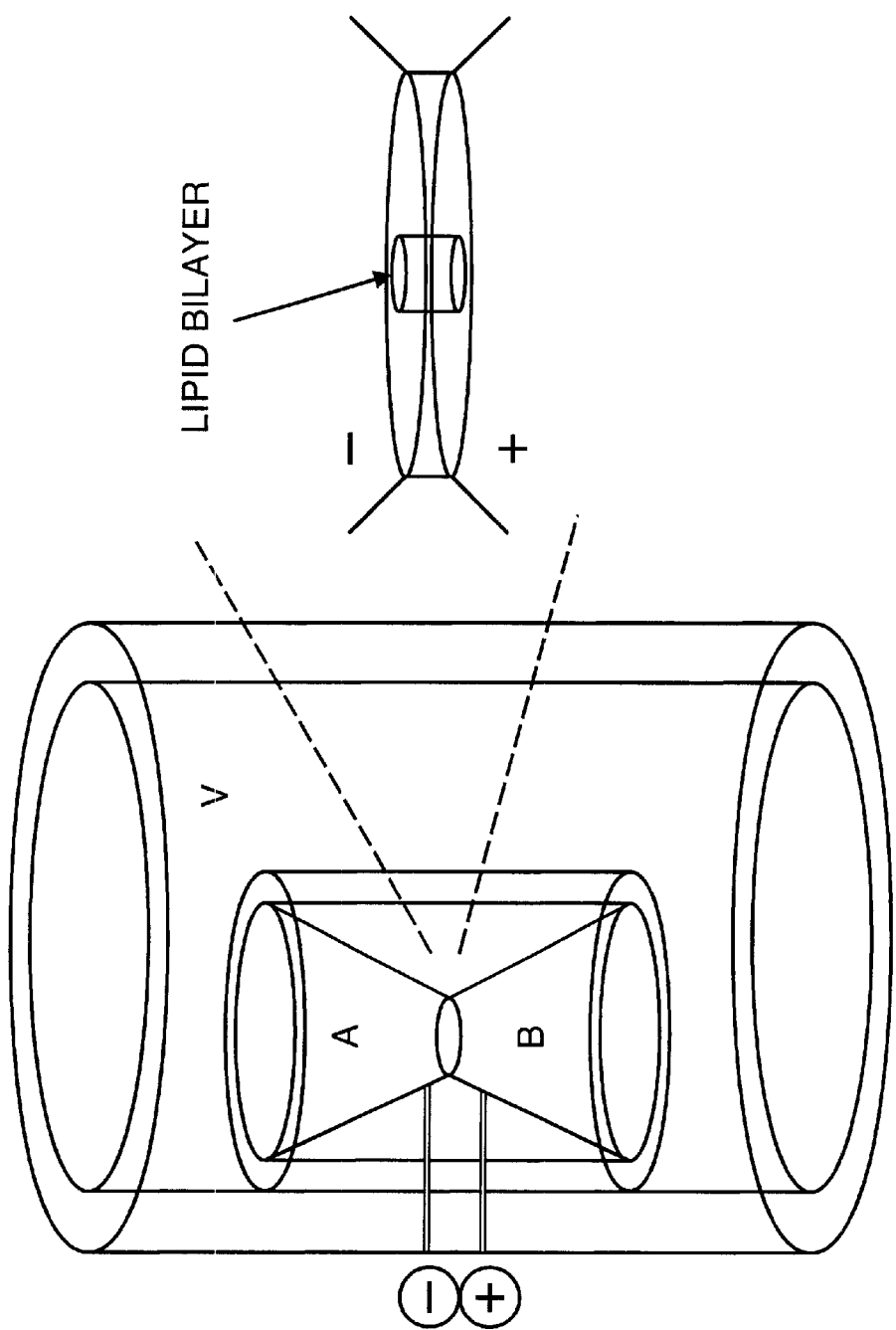
FIG. 3 is a single chamber implementation of the invention as described in Example 2.

This Example describes use of the o:-hemolysin pore system of Example 1 in an arrangement that utilizes only a single pool of liquid containing medium and allows improved optical analysis. As shown in FIG. 3, a substantially conical device is introduced inside the chamber. The chamber is then filled with a conductive medium. The lipid bilayer is formed at the vertex of the cone (see inset of FIG. 3). Into the open end of the cone (e.g., the larger opening with no lipid bilayer), would be introduced the polymer (i.e., nucleic acid polymer) to be characterized. An electric field would be applied allowing the negatively charged nucleic acid polymer to be pulled through the α-hemolysin pore. This will allow the monomers of the polymer to interact with the optical agent attached to the α-hemolysin pore in a serial manner over time.

Without the two pools of medium and the interface between them, optical analysis of the changes in the optical agent as it interacts with the monomers of the polymer will be improved.

Example 3—Sequencing a Nucleic Acid with an Exonuclease and a Fluorescence Reporter Group This Example describes the use of an optical agent associated with an exonuclease to determine the nucleotide sequence of a single stranded nucleic acid polymer. Those of ordinary skill in the art will recognize that any exonuclease may be utilized so long as it may be linked to an optical agent. Preferably, the optical agent comprises a single fluorophore and is attached to the exonuclease at a position sufficiently close to its nucleic acid binding site that nucleotides pass through the fluorophore's interaction volume as they are released from the polymer.

For example, Jezewska et al. (*J. Biol. Chem.* 273(17): 10515, 1998, incorporated herein by reference) have described a hexameric exonuclease whose crystal structure has been determined so that its nucleic acid binding site is well characterized. In one version of this embodiment of the invention, a single copy of the Jezewska et al. exonuclease is attached to a solid support, for example via a biotin/avidin linkage or other means known in the art. The exonuclease is also linked to a single fluorophore, for example through modification of the amino acid sequence of the 12 kDa exonuclease subunit in the vicinity of (i.e., within 1–10 Angstroms of) the nucleotide exit site so that a single cysteine is present, followed by coupling of that cysteine with a fluorophore.

Excitation of fluorescence, and subsequent measurements of fluorescence quenching in the presence of the nucleotide may be accomplished as described in Example 1.

Although this exonuclease system represents a useful embodiment of the present invention, it may not be as effective as a pore-based sequencing system such as those described in Examples 1 and 2 since enzymatic processes like digestion are typically much slower (tens to hundreds of bases per second) than the transfer of a nucleic acid molecule through a pore (a few microseconds per base). Furthermore, low enzyme processivity may reduce the length of sequence that can be determined.

Example 4—Synthetic Pore

This example describes the use of a synthetic pore rather than a natural pore like α-hemolysin as discussed in Example 1. In this embodiment, the polymer to be characterized will be passed through a pore in a membrane which would be created in number of ways including laser ablation, chemical etching, mechanical means, etc.

In a preferred embodiment of the invention, Poretics polycarbonate track-etch (PCTE) membrane filters from Osmonics (Minnetonka, Minn.) are used. These filters are created by exposing a thin polycarbonate film to collimated, charged particles in a nuclear reactor and thereby leaving sensitized tracks in the material. The material is then exposed to chemicals which etch out the tracks to leave uniform, cylindrical pores. Rather than a lipid bilayer and α-hemolysin pore as in example 1, PCTE membrane filters are used after the optical agent has been attached by chemical means to the pores in the membrane. The optical agent could be attached within the pore or on either side of the pore. The polymer (i.e., nucleic acid polymer) is passed through a pore in the membrane using an electric field. Changes in fluorescence decay time are then measured as monomers of the polymer pass by the fluorophore as in Example 1. This method avoids the use of biological substances to create the pore and may be optically cleaner than a biological system.

Example 5—Arrays

As mentioned above, certain preferred embodiments of the invention involve arrays of assay chambers. The present Example describes particular embodiments of such arrays utilizing the α-hemolysin system of Example 1.

In one embodiment, the array comprises a membrane having multiple 1–2 micron holes in it (e.g., introduced by, for example, laser ablation or track etching for sufficient length of time) and having the membrane clamped between two pieces of material having arrays of holes. The 1–2 micron holes of the membrane are aligned with the holes in the material clamping it. Lipid bilayers are applied to the holes in the membrane, and then each well is used as an assay chamber.

In another preferred embodiment, an array of conical members such as those described in Example 2 and depicted in FIG. 2 is stamped into an existing lipid bilayer, so that individual bilayers are formed across the points of the conical members. This array is then fitted onto an array of wells containing cathodes and anodes, so that arrayed assay chambers are created. In preferred embodiments, the conical members are constructed and arranged to allow passage of fluid from the well into the cone of the conical member so that a single reaction chamber is created. In particularly preferred embodiments, this fluid passage may temporarily be blocked (e.g., by raising the conical members) so that the integrity of the lipid bilayer and (α-hemolysin pore may be tested as described in Example 1, and then the liquid volumes may be connected prior to introduction of nucleic acid into the system. This strategy has the advantage of allowing pressure to be equalized on both sides of the pore before the nucleic acid is analyzed.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

APPENDIX A

Table of Fluorophores

| Fluorophore | MW | Em (nm) | Abs (nm) | Notes |
|---|---|---|---|---|
| Alexa Fluor 350 | | 442 | 346 | |
| Alexa Fluor 430 | | 539 | 433 | Large Stokes shift |
| Alexa Fluor 488 | | 519 | 495 | Bright and photostable fluorescein substitute; fluorescence output unmatched by any other spectrally similar dye; pH-insensitive fluorescence between pH 4 and 10; ideal for excitation by the 488 rm spectral line of the argon-ion laser |
| Alexa Fluor 532 | | 554 | 531 | Bright and photostable dye with spectra intermediate between those of fluorescein and tetramethylrhodamine; fluorescence output unmatched by any other spectrally similar dye; pH-insensitive fluorescence between pH 4 and 10; ideal for excitation by the 532 rm frequency-doubled principal line output of the Nd:YAG laser |
| Alexa Fluor 546 | | 575 | 556 | Bright and photostable tetramethylrhodamine or Cy3 substitute; fluorescence output unmatched by any other spectrally similar dye; pH-insensitive fluorescence between pH 4 and 10; less prone to aggregation than tetra-methylrhodamine; ideal for excitation by the 546 rm spectral line of the mercury-arc lamp |
| Alexa Fluor 568 | | 603 | 578 | Bright and photostable Lissamine rhodamine B substitute; fluorescence output unmatched by any other spectrally similar dye; pH-insensitive fluorescence between pH 4 and 10; ideal for excitation by the 568 rm spectral line of the Ar—Kr laser |
| Alexa Fluor 594 | | 617 | 590 | Bright and photostable Texas Red dye substitute; fluorescence output unmatched by any other spectrally similar dye; pH-insensitive fluorescence between pH 4 and 10; ideal for excitation by the 594 rm spectral line of the He—Ne laser |
| AMCA | | 448 | 349 | Widely used lue fluorescent labeling dye; compact structure |
| Aminocoumarin | | 445 | 350 | |
| BODIPY 493/503 | | 506 | 500 | pH-insensitive fluorescence; narrow spectral bandwidth; higher 488 nm absorptivity than the BODIPY FL fluorophore |
| BODIPY-FL | 512 | 513 | 505 | BODIPY substitute for fluoroscein; pH-insensitive Fluorescence; |

APPENDIX A-continued

Table of Fluorophores

| Fluorophore | MW | Em (nm) | Abs (nm) | Notes |
|---|---|---|---|---|
| BODIPY FL Br$_2$ | | 548 | 533 | narrow spectral bandwidth; useful for automated DNA sequencing[6] Useful for DAB photoconversion |
| BODIPY R6G | | 550 | 528 | BODIPY substitute for rhodamine 6G; pH-insensitive fluorescence; narrow spectral bandwidth; useful for automated DNA sequencing[6] |
| BODIPY 530/550 | | 554 | 534 | pH-insensitive fluorescence; narrow spectral bandwidth |
| BODIPY TMR | | 574 | 542 | BODIPY substitute for TMR; pH-insensitive fluorescence; narrow spectral bandwidth |
| BODIPY 558/568 | | 569 | 558 | pH-insensitive fluorescence; narrow spectral bandwidth |
| BODIPY 564/570 | | 571 | 565 | pH-insensitive fluorescence; narrow spectral bandwidth; useful for automated DNA sequencing[7] |
| BODIPY 576/589 | | 590 | 576 | pH-insensitive fluorescence; narrow spectral bandwidth |
| BODIPY 581/591 | | 592 | 584 | pH-insensitive fluorescence; narrow spectral bandwidth; useful for automated DNA sequencing[7] |
| BODIPY TR | | 617 | 589 | BODIPY substitute for Texas Red fluorophore; pH-insensitive fluorescence |
| BODIPY 630/650 | | 640 | 625 | pH-insensitive fluorescence; ideal for excitation by the 633 rm spectral line of the He—Ne laser |
| BODIPY 650/665 | | 660 | 646 | pH-insensitive fluorescence; longest-wavelength BODIPY dye available; ideal for excitation by the 647 rm spectral line of the krypton-ion laser |
| Cascade Blue dye | 423 | 420 | 400 | Resistant to quenching upon protein conjugation; water soluble |
| Cascade Yellow dye | | 545 | 402 | Large Stokes shift; high molar absorptivity |
| Cl-NERF | | 544 | 518 | pH-sensitive fluorescence between pH 3–5 |
| Dansyl | | 520[1] | 340 | Environment-sensitive fluorescence; large Stokes shift |
| Dapoxy 1 dye | | 551[1] | 373 | Environment-sensitive fluorescence; large Stokes shift |
| Dialkyl-aminocoumarin | | 470[2] 475[3] | 375 435 | Longer-wavelength alternatives to AMCA |
| 4',5'-Dichloro-2',7'-dimethoxy-fluorescein | | 550 | 522 | Succinimidyl ester derivative (6-JOE, SE; C-6171) is widely used for automated DNA sequencing[7–9] |
| 2',7'-Dichloro-fluorescein | | 532 | 510 | pH-insensitive fluorescence at pH > 6 |
| DM-NERF | | 542 | 515 | pH-sensitive fluorescence between pH 4.5–6.5 |
| Eosin | | 544 | 524 | Phosphorescent |
| Eosin F$_3$S | | 542 | 535 | Photostable eosin derivative useful for DAB photoconversion |
| Erythrosin | | 555 | 530 | Phosphorescent |
| Fluoroscein | 519 | 518 | 494 | Widely used; pH sensitive; prone to bleaching |
| Hydroxycoumarin | 386 | 445[4] 455[5] | 385 360 | pH-sensitive fluorescence; compact structure |
| Isosulfan blue | | none | 650 | Nonfluorescent photosensitizer |
| Lissamine Rhodamine B | 590 | 590 | 570 | Photostable; Optimal for 568 nm excitation |
| Malachite green | | none | 630 | Nonfluorescent photosensitizer |
| Marina Blue dye | | 460 | 365 | Strongly fluorescent at neutral pH, unlike hydroxycoumarin; optimal for 365 nm excitation of the mercury-arc lamp |
| Methoxycoumarin | 410 | 405 | 340 | pH insensitive alternative to hydroxycoumarin |
| Naphtho-fluorescien | | 675 | 605 | Very long-wavelength excitation and emission; pH-sensitive fluorescence |
| NBD | | 535 | 465 | Environmentally-sensitive fluorescence; compact structure |
| Oregon Green 488 | | 524 | 496 | Photostable fluorescein substitute; pH-insensitive fluorescence at pH > 6 |
| Oregon Green 500 | | 522 | 503 | Photostable fluorescein substitute; pH-insensitive fluorescence at pH > 6 |
| Oregon Green 514 | | 530 | 511 | Exceptionally photostable; pH-insensitive fluorescence at pH > 6 |
| Pacific Blue dye | | 455 | 410 | Strongly fluorescent at neutral pH, unlike hydroxycoumarin |
| Pyrene | | 378 | 345 | Long excited state lifetime; spectral shifts due to excimer emission |
| PyMPO | | 570 | 415 | Large Stokes shift |
| Rhodamine 60 | | 555 | 525 | Absorption matched for 514 nm excitation |
| Rhodamine Green dye | | 527 | 502 | Photostable fluorescein substitute; pH-insensitive fluorescence |
| Rhodamine Red dye | | 590 | 570 | Rhodamine Red-X succinimidyl ester generally yields higher fluorescence per attached dye than Lissamine |

APPENDIX A-continued

Table of Fluorophores

| Fluorophore | MW | Em (nm) | Abs (nm) | Notes |
|---|---|---|---|---|
| Rhodol Green dye | | 525 | 499 | rhodamine B sulfonyl chloride and is more stable in $H_2O$ Photostable fluorescein substitute; pH-sensitive fluorescence between 4.5–6.5 |
| 2',4',5',7'-Tetra-bromosulfone fluorescein | | 544 | 528 | Eosin derivative useful for DAB photoconversion |
| Tetramethyl-rhodamine (TMR) | | 580 | 555 | pH-insensitive fluorescence; photostable; prone to aggregation; succinimidyl ester derivative (6-RAMRA, SE; C-6123) is widely used for automated DNA sequencing[7–9] |
| Texas Red | | 615 | 615 | 595 |
| X-Rhodamine | 576 | 605 | 580 | Widely used in automated DNA sequencing[7–9] |

The absorption (Abs) and fluorescence emission (Em) maxima listed in the above table are for the goat anti-mouse IgG or dextran conjugates in aqueous buffer.
[1]Emission spectra of dansyl and Dapoxyl protein conjugates may vary considerably depending on the dye attachment site and the degree of labeling;
[2]Spectral maxima for D-374;
[3]Spectral maxima for D-1412;
[4]Spectral maxima for H-1193;
[5]Spectral maxima for H-1411;
[6]Science 271, 1420 (1996);
[7]Anal. Biochem. 223, 39 (1994);
[8]Nucleic Acids Res. 20, 2471 (1992);
[9]Proc. Natl. Acad. Sci. USA 86, 9178 (1989).

Reactive and Conjugated probes

| | | |
|---|---|---|
| Aminocoumarin | 445 | 350 |
| Lucifer yellow | 528 | 425 |
| NBD | 539 | |
| R-Phycoerythrin (PE) | 478 | 480; 565 |
| PE-Cy5 conjugates | 670 | 480; 565; 650 |
| PE-Cy7 conjugates | 767 | 480; 565; 743 |
| Red 613 | 613 | 480; 565 |
| Cy3 | 565, 615 | 512; 552 |
| TRITC | 572 | 547 |
| PerCP | 675 | 490 |
| Cy5 | 670 | 625–650 |
| Cy7 | 767 | 743 |
| Allophycocyanin (APC) | 660 | 650 |
| TruRed | 695 | 490, 675 |
| APC-Cy7 conjugates | 767 | 650; 755 |

Nucleic acid probes

| | | |
|---|---|---|
| Hoechst 33342 | 483 | 343 |
| DAPA | 455 | 345 |
| Hoechst 33258 | 478 | 345 |
| Chromomycin A3 | 575 | 445 |
| Mithramycin | 575 | 445 |
| Thiazole Orange | 480 | 453 |
| YOYO-1 | 509 | 491 |
| Ethidium Bromide | 620 | 493 |
| Acridine Orange | 530/640 | 503 |

APPENDIX A-continued

Table of Fluorophores

| Fluorophore | MW | Em (nm) | Abs (nm) | Notes |
|---|---|---|---|---|
| TOTO-1, TO-PRO-1 | 533 | | 509 | |
| Propidium Iodide (PI) | 617 | | 536 | |
| TOTO-3, TO-PRO-3 | 661 | | 642 | |

Cell function probes

| | | | | |
|---|---|---|---|---|
| Indo-1 | 490/405 | | 361/330 | |
| Fluo-3 | 526 | | 506 | |
| 2'7'Dichorodi-hydrofluorescein (DCFH) | 535 | | 505 | |
| Dihydrorhod-amine 123 (DHR) | 534 | | 505 | |
| SNARF | 587/635 | | 548/579 | |

Green Fluorescent Proteins

| | | | | |
|---|---|---|---|---|
| Y66F | 508 | | 360 | |
| Y66H | 442 | | 360 | |
| Y66W | 485 | | 436 | |
| Wild Type | 508, 503 | | 396, 475 | |
| S65A | 504 | | 471 | |
| S65C | 507 | | 479 | |
| S65L | 510 | | 484 | |
| S65T | 511 | | 488 | |

Other Probes

| | | | | |
|---|---|---|---|---|
| Monochloro-bimane | 461 | | 380 | |
| Calcein | 517 | | 496 | |

Legend:
Ex: Peak excitation wavelength (nm)
Em: Peak emission wavelength (nm)
MW: Molecular weight

What is claimed is:

1. An apparatus comprising:

an alpha-hemolysin pore;

an optical agent associated with the pore, the optical agent being selected and arranged so that, when a nucleic acid polymer is passed through the pore, each base of the polymer interacts with the optical agent in a characteristic way, resulting in a characteristic change in an optical property of the optical agent; and a detector selected and arranged to detect the characteristic changes so that, as the nucleic acid polymer passes through the pore, the bases are individually identified by the detected characteristic changes.

2. An apparatus comprising:

a biological pore defining a channel dimensioned to accept a nucleic acid polymer so that a single nucleic acid strand passes in linear fashion through the pore;

an optical agent associated with the pore, the optical agent being selected and arranged to that, when a nucleic acid polymer is passed through the pore, each base of the polymer interacts with the optical agent in a characteristic way, resulting in a characteristic change in an optical property of the optical agent; and a detector selected and arranged to detect the characteristic changes so that, as the nucleic acid polymer passes through the pore, the bases are individually identified by the detected characteristic changes.

3. An apparatus comprising:
- a biological pore defining a channel dimensioned to accept a nucleic acid polymer so that a single nucleic acid strand passes in linear fashion through the pore;
- an optical agent associated with the pore, the optical agent being selected and arranged to that, when an unlabeled nucleic acid polymer is passed through the pore, each nucleotide residue interacts with the optical agent in a characteristic way, resulting in a characteristic change in an optical property of the optical agent; and
- a detector selected and arranged to detect the characteristic changes so that, as the nucleic acid polymer passes through the pore, the -nucleotide residues are individually identified by the detected characteristic changes.

4. An apparatus comprising:
- a pore defining a channel dimensioned to accept a nucleic acid polymer so that the nucleic acid polymer passes in linear fashion through the pore;
- an optical agent associated with the pore, the optical agent being selected and arranged to interact with individual monomers of the nucleic acid polymer in a characteristic way, resulting in a characteristic change in an optical property of the optical agent; and
- a detector selected and arranged to detect the characteristic changes so that, as the nucleic acid polymer passes through the pore the monomers are individually identified in their linear order by the detected characteristic changes.

5. The apparatus of claim 1, 2, 3, or 4, wherein the optical agent comprises a fluorophore.

6. The apparatus of claim 5, wherein the characteristic change comprises quenching of fluorescence.

7. The apparatus of claim 6, wherein the quenching results from electron transfer and the pore and optical agent are arranged with respect to one another so that, when a polymer passes through the pore, its monomers pass within 10–100 Angstroms of the optical agent.

8. The apparatus of claim 1, 2, 3, or 4 wherein the optical agent has sufficient stability to allow analysis of polymers at least 1000 monomer units long.

9. The apparatus of claim 1, 2, 3, or 4, wherein the pore comprises at least one protein.

10. The apparatus of claim 1, 2, 3, or 4 wherein the optical agent comprises a quantum dot.

11. The apparatus of claim 1, 2, 3, or 4, wherein the optical agent is linked to the pore through covalent or non-covalent interactions.

* * * * *